United States Patent [19]

Oechsle

[11] Patent Number: 4,791,807

[45] Date of Patent: Dec. 20, 1988

[54] APPARATUS FOR DETERMINING THE RELATIVE HARDNESS AND ABRASION RESISTANCE OF INDUSTRIAL FILM COATINGS AND LININGS

[76] Inventor: S. John Oechsle, 3595 Netherfield Rd., Philadelphia, Pa. 19129

[21] Appl. No.: 926,536

[22] Filed: Nov. 4, 1986

[51] Int. Cl.⁴ .............................................. G01N 3/46
[52] U.S. Cl. ............................................ 73/78; 73/7; 73/150 R; 30/164.9
[58] Field of Search .............. 73/78, 7, 8 L, 85, 150 R, 73/150 A, 104; 33/169 F; 30/164.9

[56] References Cited

U.S. PATENT DOCUMENTS

| | | | |
|---|---|---|---|
| 2,130,269 | 9/1938 | Dietert | 73/78 |
| 2,436,435 | 2/1948 | Kent | 73/85 |
| 2,801,540 | 8/1957 | Rondeau | 73/78 X |
| 3,069,892 | 12/1962 | Gjertsen | 73/78 X |
| 3,289,458 | 12/1966 | Deichert et al. | 73/78 X |
| 3,785,198 | 1/1974 | Heetman | 73/78 |

OTHER PUBLICATIONS

"Modern Scratch Hardness Methods"; *Instruments*, vol. 10, pp. 286–288; Nov. 1937; S. R. Williams.

*Primary Examiner*—Thomas P. Noland
*Attorney, Agent, or Firm*—Robert S. Bramson

[57] ABSTRACT

A novel apparatus for determining the relative hardness and abrasion resistance of industrial film coatings and linings is disclosed. In its preferred form, the apparatus comprises a rigid handle incorporating a pre-set angle between its flat lower surface and a flexible spring blade attached at one end to the handle, and a scoring stylus attached at the other end of the spring blade. By placing the bottom of the handle on the surface of the film coating or lining whose relative hardness and abrasion resistance is to be determined, the spring blade is caused to deflect and thereby exert a constant and predetermined force through the scoring stylus onto the film coating or lining. By drawing or pulling the handle across the surface of the film coating or lining while maintaining the lower surface of the handle in complete contact with the film coating or lining, the scoring stylus creates a scratch on the surface of the film coating or lining. Depending upon the cross-sectional configuration of the scoring stylus used, the depth of the scratch created by the scoring stylus can be directly measured, or can be indirectly measured by measuring the width of the scratch and geometrically relating the depth to the measured width. Having determined the depth of the scratch created by the scoring stylus on the surface of the film coating or lining, a quantitative determination of the relative hardness and abrasion resistance of the film coating or lining is obtained.

6 Claims, 1 Drawing Sheet

APPARATUS FOR DETERMINING THE RELATIVE HARDNESS AND ABRASION RESISTANCE OF INDUSTRIAL FILM COATINGS AND LININGS

BACKGROUND OF INVENTION

1. Field of the Invention

The invention relates to the determination of the relative hardness and abrasion resistance of industrial film coatings and linings. Such coatings and linings traditionally have been applied to the interior or exterior surfaces of various metallic and non-metallic industrial structures, containers, vessels, pipes, and the like. The purpose of such film coatings and linings is to prevent or retard the corrosion or deterioration of the surfaces to which they are applied. The invention disclosed relates particularly to the determination of the relative hardness and abrasion resistance of film coatings and linings applied to such surfaces.

2. Description of the Prior Art

When industrial film coatings or linings are applied to various metallic and non-metallic surfaces in order to protect against deterioration or corrosion of such surfaces, it often is considered desirable to assess the prospective effectiveness of a particular film coating or lining by determining its relative hardness and abrasion resistance.

Prior to the disclosed invention, there existed two generally used methods for determining the relative hardness and resistance to abrasion of industrial film coatings and linings. In the first method, a readily available hard object is "scratched" along the film coating or lining surface of interest, and human judgment is used to evaluate the depth and width of the created scratch, resulting in a subjective evaluation of the relative hardness and abrasion resistance of the film coating or lining. These "scratches" have been created by such means as: (1) applying a quarter to the film coating or lining surface and drawing or pulling the quarter across the surface; (2) applying a human fingernail to the film coating or lining surface and drawing or pulling the human fingernail across the surface; or (3) applying pencils of various hardnesses to the film coating or lining surface and drawing or pulling a pencil across the surface, as in the ASTM 3363 Pencil Test.

The foregoing means of determining, in the field, the relative hardness and abrasion resistance of industrial film coatings and linings are disadvantageous because of the numerous variables associated with each method, including the amount of force applied to the scratching implement by the test operator, the angle or attitude of the scratching implement as applied to the particular film coating or lining surface, and the hardness or sharpness of the scratching implement itself. These variables result in random, uncontrolled and non-repeatable determinations of relative hardness and abrasion resistance.

A second method previously used to determine the relative hardness and abrasion resistance of industrial film coatings and linings involves the use of various sophisticated electrical or electronic testing devices. Although such devices are capable of producing repeatable and non-random results, such devices generally are not suitable for use "in the field," i.e., at the location for use of the object of interest, but rather must be used in the controlled context and environment of a scientific laboratory or workshop. In addition, these sophisticated devices generally can only be used on horizontal surfaces, and cannot be used to determine the relative hardness and abrasion resistance of film coatings or linings applied to vertical or partially inclined surfaces.

SUMMARY OF THE INVENTION

The invention is directed to an apparatus for determining the relative hardness and abrasion resistance of industrial film coatings applied to the interior or exterior surfaces of various metallic and non-metallic structures, containers, vessels, tanks, pipes, and the like. The invention is an apparatus comprising a handle incorporating a pre-set angle between its lower surface and an elongated, flat, flexible spring blade attached at one end to the handle, and a scoring stylus attached to other end of the spring blade. The spring blade is of predetermined length and spring constant, depending upon the general range of relative hardnesses and abrasion resistances to be determined.

The invention is used by causing the substantially planar bottom of the handle to be placed in contact along substantially its entire length with the surface of the film coating or lining whose relative hardness or resistance to abrasion is to be determined, thereby causing the spring blade to deflect and exert a constant, predetermined force through the scoring stylus onto the subject surface. The handle is then drawn or pulled by the user across the surface, causing the scoring stylus to create a scratch of particular depth and width, which will depend on the physical characteristics of the film coating or lining surface. The depth of the scratch may be measured directly by known techniques, or, depending upon the planar cross-sectional configuration of the scoring stylus used, the depth of the scratch may be indirectly measured by first measuring the width of the scratch and thereafter geometrically relating such width to the desired depth.

Having measured the depth of the scratch, a quantitative determination of the relative hardness and abrasion resistance of the film coating or lining is obtained.

OBJECT OF THE INVENTION

It is the object of this invention to provide an improved apparatus capable of performing controlled, standardized, and repeatable determinations of the relative hardness and abrasion resistance of industrial film coatings and linings.

It is the further object of this invention to enable the foregoing determinations of relative hardness and abrasion resistance to be performed under "field" conditions and upon coated or lined surfaces that may be horizontal, vertical, or partially inclined.

DETAILED DESCRIPTION OF THE INVENTION

The invention relates to an apparatus for easily and quickly determining the relative hardness and abrasion resistance of industrial film coatings and linings applied to the interior or exterior surfaces of various metallic and nonmetallic structures, containers, vessels, pipes, and the like. It will be appreciated that, as an incident of numerous industrial processes and procedures, it often is necessary to coat or line such surfaces with appropriate film coatings or linings in order to prevent or retard the corrosion or deterioration of the surfaces. It further will be appreciated that, after a film coating or lining has been applied to a particular surface, it often is desirable to determine the relative hardness and abrasion resistance of the film coating or lining in order to assure its effectiveness. The disclosed prevention permits such determination of relative hardness and abrasion resistance in a controlled, standardized, and repeatable manner.

Figure 1:
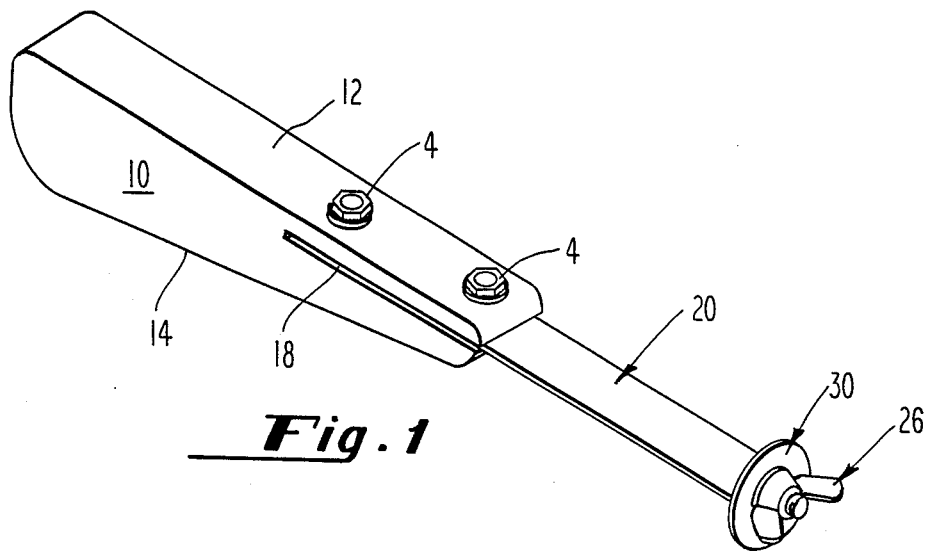
FIG. 1 is a perspective view of the apparatus of the invention.

Viewing FIG. 1, it will be seen that the handle 10 of the invention incorporates a pre-set angle between its upper and lower surfaces 12 and 14. Attached to the handle 10 is an elongated, flat, and flexible spring blade 20, that makes a predetermined angle with respect to the lower surface 14 of the handle 10 when the spring blade 20 is in an undeflected position (shown in solid lines in FIG. 2). The spring blade 20 is of a predetermined length and spring constant that will exert the desired constant force on the subject film coating or lining through the scoring stylus 30, as hereinafter described. By substituting spring blades of different lengths and/or spring constants, forces of different magnitudes can be applied to different film coatings or linings, depending upon the general range of relative hardnesses and abrasion resistances expected. The particular spring material, spring constant and length can be varied widely within the purview of this invention and readily selected by the skilled artisan to suit the needs of particular uses of the invention.

Figure 2:
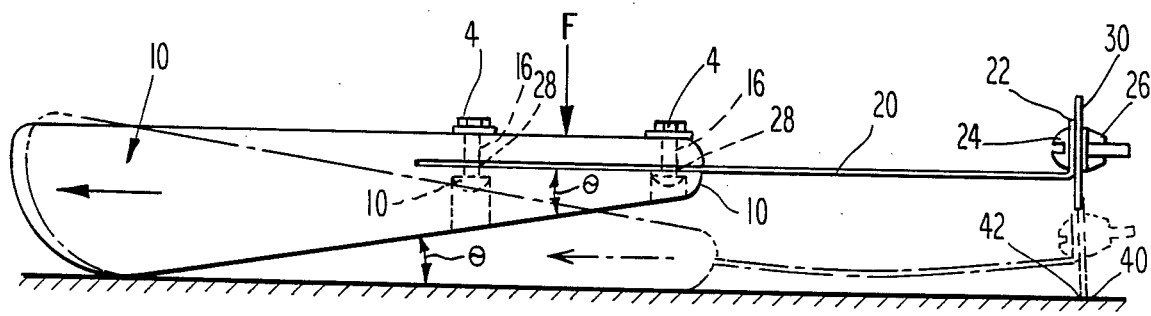
FIG. 2 is a side elevational view of an apparatus of the invention, including a view in phantom of the invention as applied to a film coating or lining whose hardness or abrasion resistance is to be determined.

Viewing FIG. 2, it will be seen that the end of the spring blade 20 not attached to the handle 1 has a perpendicular flange 22, attached to which flange 22 is a scoring stylus 30. The scoring stylus 30 is rigidly and removably attached to the flange 22 by means of wing-nut 26 threadably engaged to a machine screw 24. The blade 20 is made of rigid material, such as wood or plastic, and includes a slot 18 in which an end of the blade 20 is seated. The spring blade 20 is rigidly and removably attached to the handle 10 by means of two nuts 12 threadably engaged to two machine screws 12 and extend through suitable apertures 16 in the handle and 28 in the blade 20. The scoring stylus 30 projects below the proximate end of handle 10, so that the spring force projects the stylus against the surface being tested when the handle is pressed against the surface, as seen in FIG. 2 in phantom.

The bottom 14 of the handle 10 is seen to be substantially flat and tapers inwardly with respect to the blade 20, and makes an acute angle theta with respect to the blade.

Figure 3:
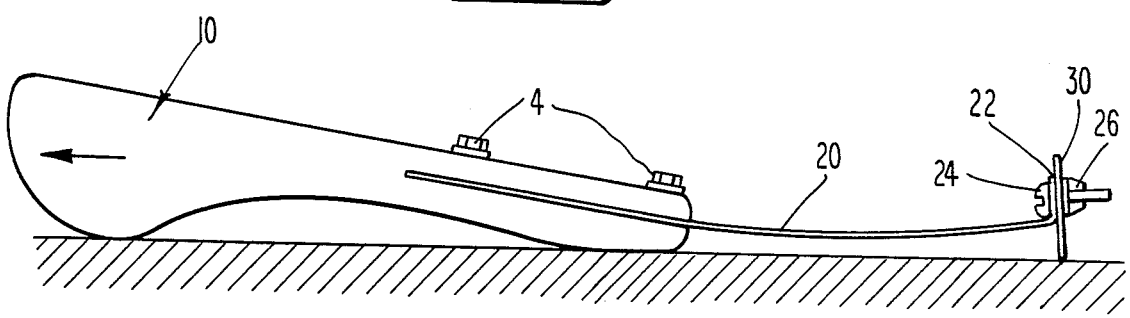
FIG. 3 a is a side elevational view of an apparatus of the invention in use, and showing an alternative shape of the bottom surface of the handle.

Although the bottom 14 is shown as flat, it may have other shapes, as for example the curved shape shown in FIG. 3, so long as it can lie rigidly on a surface as it is drawn along the surface in the direction of the arrows shown in FIGS. 2 and 3.

When it is desired to determine the relative hardness and abrasion resistance of a particular film coating or lining 40, the lower surface 4 of the handle 10 is placed in contact along its entire length with the surface of film coating or lining 40 by means of a force exerted on the upper surface of the handle 10 by the test operator in a direction perpendicular to the film coating or lining surface 40, thereby causing the lower surface 14 of the handle 10 to come into contact with the film coating or lining surface 10 along the entire length of the lower surface of the handle 1, as seen in FIG. 2 in phantom. As the lower surface of the handle 10 is brought into contact along its entire length with the film coating or lining surface 40, the spring blade 20 is caused to deflect, thereby exerting a predetermined force through the scoring stylus 30 onto the surface of film coating or lining 40 at the contact point 42 between the scoring stylus 30 and the film coating or lining surface 40 (shown in FIG. 2 in phantom).

Continuing to view FIG. 2, after the described force has been applied by the test operator to the handle 10, thereby causing the spring blade 20 to deflect and exert the resultant predetermined force through the scoring stylus 30 onto the surface of the film coating or lining 4 at the contact point 8, a quantitative evaluation of the relative hardness and abrasion resistance of film coating o lining 40 is obtained by measuring the depth of a scratch created by drawing or pulling the handle 10 in the direction of the arrow along the surface of the film coating or lining 40. The scratch is created by the scoring stylus 30 on the surface of the film coating or lining 40 at the contact point 42 between the scoring stylus 30 and the subject surface 40.

Figure 4:
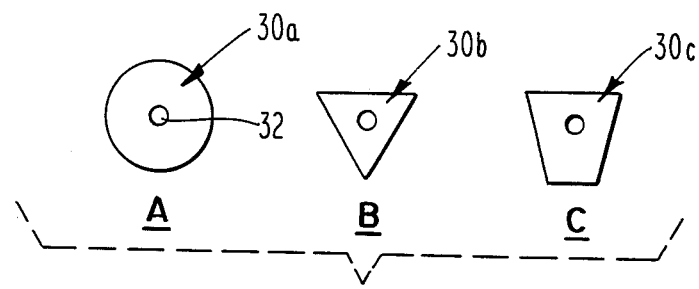
FIG. 4 is a front elevational view of three different scoring styli suitable for use in an apparatus of the invention.

Now, viewing particularly FIG. 4, it will be seen that scoring stylus A has a round shape, scoring stylus B has the shape of an equilateral triangle; and scoring stylus C has the shape of a truncated isosceles triangle. When the handle 10 is drawn or pulled across the surface of the film coating or lining 40, it will be seen that the scratch created by the scoring stylus 30 will be of a particular depth and width, depending upon the planar cross-sectional configuration of the scoring stylus 30 used.

The depth of the scratch created by the scoring stylus 30 on the surface of the film coating or lining 40 may be measured by either of two methods:

First, the depth of the scratch may be directly measured by using a standard field thickness tester. Such standard field thickness tester may be of the type commonly known as an "inspector gauge" or "microtest."

A second method of measuring the depth of the scratch created by the scoring stylus 30 created on the surface of the film coating or lining 40 requires the initial measurement of the width of the scratch, using a known instrument with a magnifier and reticle, most appropriately graduated in thousandths of an inch. Depending upon the cross-sectional configuration of the scoring stylus 30 used, the resulting width measurement may be geometrically related to the desired depth of the scratch. Thus, for example, where a scoring stylus 30b with a planar cross-sectional configuration in the shape of an equilateral triangle is used, the desired depth of the scratch can readily be determined under well established principles of elementary geometry, since the desired depth of the scratch will be the height of the equilateral triangle and the measured width of the scratch will be the base of such equilateral triangle.

In similar fashion, using well established and principles of elementary geometry, the desired depths of scratches created by scoring styli of other cross-sectional planar configurations, as shown in FIG. 4, may be related to and obtained from the directly measured widths of such scratches.

Having either directly or indirectly measured the depth of the scratch created by the scoring stylus 30 on the film coating or lining surface 40, a quantitative evaluation of the relative hardness and abrasion resistance the film coating or lining is obtained.

There are three principal benefits of the invention.

First, depending upon the general range of relative hardnesses or abrasion resistances expected, the spring blade 2 may be of a specific length and temper, thereby allowing the exertion of a constant and predetermined force through the scoring stylus 30 onto the surface of film coating or lining 40. This eliminates operator-induced variables and results in standardized, controlled, and repeatable determinations of the relative hardness and abrasion resistance of film coatings or linings Second, the invention may be used "in the field" at the actual, real-time location of the film coating or lining 40 whose relative hardness and abrasion resistance is to be determined. The invention is not restricted to use in a laboratory or work shop environment.

Third, the invention may be used to determine the relative hardness and abrasion resistance of film coatings or linings applied to horizontal, vertical, or partially inclined surfaces.

It will be appreciated that the disclosed invention may be modified without departing from its spirit and scope. Thus, the shape and material of the handle, size and material of the blade, and shape of the styles, may be varied widely without departing from the spirit and scope of the invention.

I claim:
1. An apparatus for testing the relative hardness and abrasion resistance of industrial film coatings and linings, comprising:
   (a) a rigid handle having upper and lower surfaces;
   (b) an elongated, flat and flexible spring blade of predetermined length and spring constant;
   (c) means rigidly removably attaching said spring blade at one end to said handle and above the lower surface of said handle;
   (d) at least two points on said lower handle surface defining an acute angle with respect to said spring blade; and
   (e) a scoring stylus rigidly, dependently attached to the other end of said flexible spring blade.

2. An apparatus as set forth in claim 1, further including a means for removably attaching said spring blade to said handle, and said scoring stylus projecting beneath the proximate end of said handle when the spring blade is in an horizontal position.

3. An apparatus as set forth in claim 1, wherein said spring blade has a perpendicular flange at the end not attached to said handle, and a means for removably attaching said scoring stylus to said perpendicular flange.

4. An apparatus as set forth in claims 1 or 3, wherein said scoring stylus has a planar cross-sectional configuration in the shape of a circle.

5. An apparatus as set forth in claims 1 or 3, wherein said scoring stylus has a planar cross-sectional configuration in the shape of an equilateral triangle.

6. An apparatus as set forth in claims 1 or 3, wherein said scoring stylus has a planar cross-sectional configuration in the shape of a truncated equilateral triangle.

* * * * *